United States Patent [19]

Shaw

[11] 4,184,973
[45] Jan. 22, 1980

[54] HAIR GROOMING AID CONTAINING FIBRILLATABLE POLYTETRAFLUOROETHYLENE RESIN

[75] Inventor: Glen A. Shaw, Lyndhurst, Ohio

[73] Assignee: The Harshaw Chemical Company, Cleveland, Ohio

[21] Appl. No.: 832,245

[22] Filed: Sep. 12, 1977

Related U.S. Application Data

[60] Division of Ser. No. 580,143, May 23, 1975, Pat. No. 4,047,537, which is a continuation-in-part of Ser. No. 373,585, Jun. 25, 1973, abandoned.

[51] Int. Cl.² .......................... C11D 1/00; C11D 7/30; A61K 7/06
[52] U.S. Cl. .......................... 252/174.23; 252/DIG. 3; 252/13; 424/70; 424/83
[58] Field of Search .................... 252/89, DIG. 2, 13; 132/7; 424/70, 78, 83; 260/29.6 F

[56] References Cited

U.S. PATENT DOCUMENTS

| | | | |
|---|---|---|---|
| 2,510,112 | 6/1950 | Holbrook | 260/29.6 F |
| 2,559,752 | 6/1951 | Berry | 260/29.6 F |
| 2,587,357 | 2/1952 | McPherson | 137/625.64 |
| 2,685,707 | 8/1954 | Llewellyn et al. | 264/174 |
| 3,698,392 | 10/1972 | Vogt et al. | 128/268 |
| 3,838,064 | 9/1974 | Vogt et al. | 252/384 |
| 3,838,092 | 9/1974 | Vogt et al. | 260/33.6 F |
| 3,864,124 | 2/1975 | Breton et al. | 75/212 |

Primary Examiner—P. E. Willis, Jr.
Attorney, Agent, or Firm—James A. Lucas

[57] ABSTRACT

This invention concerns a treatment which may be applied on practically all hair and which substantially improves the cosmetic properties thereof. More particularly, it contemplates a novel hair grooming aid to beautify hair, particularly living hair, which includes as a necessary ingredient a solid phase of finely divided fibrillatable polytetrafluoroethylene (hereinafter referred to as "PTFE") resin. The invention includes a process of grooming hair comprising applying the grooming aid to hair and brushing the hair at a temperature above the transition temperature at which PTFE fibrillates to form microscopic and submicroscopic fibers, in an amount sufficient to give the hair a natural appearance and to maintain its set for a long time.

1 Claim, 2 Drawing Figures

HAIR GROOMING AID CONTAINING FIBRILLATABLE POLYTETRAFLUOROETHYLENE RESIN

CROSS-REFERENCE TO RELATED APPLICATIONS

This application is a division of applicant's copending application, Ser. No. 580,143 filed 5/23/75 (now U.S. Pat. No. 4,047,537) which is a continuation-in-part of Ser. No. 373,585 filed on June 25, 1973, now abandoned.

BACKGROUND OF THE INVENTION

It is a matter of common knowledge and experience that the hair growing on an animal, for example, the hairs on a human head, varies with the individual. This variation can be characterized as ranging from coarse hair, ultimately to fine, limp hair. Many cosmetic treatments have been proposed to correct defects in hair and to beautify it according to the prevailing styles; means are known, for example, to straighten tightly curled hair, or to curl straight hair, and to recondition hair which has been damaged by overexposure to the sun, or dyes and bleaches, and the like.

It is well known that coarse hair is more difficult to mold and style, and once styled, to keep in place, than hair of medium texture. The same problem arises with hair which is thick, that is, which is both dense and full. The term "dense" refers to the number of hairs per unit area and the term "full" refers to the common characteristic of body or fullness attributable to a mass of hair. It has been proposed to use creams, oils, alcohols, fats, such as lanolin, and styling gels, as cosmetic aids to mold thick hair. None of these is entirely satisfactory because many of them impart a "greasy" look to the hair and, with others, often an additional spray coating is needed to retain the styling. A need therefore exists to provide cosmetic grooming aids and methods to permit coarse hair and thick hair to be styled and molded more easily, to permit the styled hair to stay in place without the need to use lacquer hair sprays, and to avoid a greasy look.

On the other hand, soft-textured hair of less than medium texture, and thin hair, which is both sparse and lacks body or fullness, also presents problems in styling and keeping it in place. For example, after treatment with gummy greases and oils or alcohols, soft-textured fine hair appears to become thinner and less agreeable to the eye. To illustrate, several hairs may become "glued" into one. This problem is especially acute in so-called baby fine hair in which the thin hairs lay very close to the head. In addition, sparse hair, on men and women who have lost or begun to lose hair, due to age, or for other reasons, must be styled to take full advantage of the natural hair available. Many of the prior grooming aids mentioned above subtract body and therefore are entirely unacceptable. Thus, a need also exists to provide non-gummy means to style thin hair which will enhance the appearance thereof providing body, bulkiness and fullness to the hair.

Hair lacking elasticity also is difficult to style and manage. Hair that has been overprocessed by being chemically penetrated for tinting or bleaching, and the like, over and over again, usually is damaged and will no longer take a set. The hair just hangs. Sets are ineffective because the elasticity has been lost.

Most currently available so-called conditioners are ineffective to elasticize the hair, and this loss of elasticity detracts from the natural "springy" look of healthy hair. Particularly, with the recent emphasis on the "dry look," it is as desirable to retain the "spring" seen in normally elastic hair, as it is difficult to treat it to do so. Therefore, a need exists to provide a grooming aid and method to enhance the naturalness and elasticity of hair, and to bias the hair so treated into a natural set, which has remarkable endurance. The hair grooming aid of this invention is directed to fulfilling this need.

This invention incorporates the special use of a commercially available product commonly known as fibrillatable polytetrafluoroethylene (PTFE) which is produced and marketed by several chemical companies. Nowhere in the prior art has it been disclosed that fibrillatable PTFE is useful as a hair control agent, especially as taught in the present invention. Non-fibrillatable PTFE has been used as a component in hair-straightening formulations (see Scott U.S. Pat. No. 3,568,685) as a lubricity agent. However, this use of the most common forms of granular PTFE molding powder has no relation whatsoever to the hair net effect resulting from the unique use of fibrillatable PTFE in accordance with the present invention.

SUMMARY OF THE INVENTION

A novel hair grooming aid has been discovered in which a solid phase of finely divided fibrillatable polytetrafluoroethylene resin particles is dispersed in either a liquid phase or a "gel" phase.

It has also been discovered that solid fibrillatable PTFE particles may be used in a liquid or gel as an essential particulate ingredient which is inert with respect to any other active ingredients of a hair grooming aid.

It is a general object of this invention to provide a two-phase hair grooming aid having a solid phase of PTFE and a liquid phase; or, a solid phase of PTFE and a "gel" phase, the solid PTFE particles being dispersable in the liquid phase or gel phase, respectively.

It is a specific object of this invention to enable hair to be held in place with a hair grooming aid containing fibrillatable, solid PTFE particles which are deposited in the hair, and thereafter fibrillated in the hair, for example by brushing the hair which has been heated above room temperature, preferably to a comfortable warm temperature above about 40° C.

It is yet another specific object of this invention to provide a hair grooming aid for the treatment of hair, as described hereinabove, which imparts surprising body or fullness to the hair.

It is another specific object of this invention to provide a hair grooming aid which serves to keep hair in place, but allows the hair to retain its natural appearance.

It is a further specific object of this invention to provide a novel process for treating a mass of hair comprising depositing solid fibrillatable PTFE particles in the hair and fibrillating the particles by rubbing or brushing the hair in a dry or damp condition, while warm, sufficiently to fibrillate the particles and enable the treated hair to be held in a lasting, desirable set.

It is also a specific object of this invention to provide a hair grooming process to hold hair in place by brushing the hair so as to fibrillate PTFE particles deposited in the hair, without using a gum, wax, shellac, lacquer, oil or alcohol as an ingredient of the hair grooming composition.

It is another specific object of this invention to facilitate setting a mass of human hair, whether wet, damp or dry, by contacting the hair on the head of an individual with about a teaspoonful of a hair grooming aid containing from about 0.5 to about 1 percent by weight of a finely divided fibrillatable PTFE resin.

These and other objects, features and advantages of this hair grooming aid, and the process for treating hair with it, will become apparent to those skilled in the art from the following description of preferred forms thereof and the illustrative examples set forth herein.

BRIEF DESCRIPTION OF THE DRAWINGS

Hair, treated according to the process of this invention, is illustrated in the following photographs wherein.

DETAILED DESCRIPTION OF THE INVENTION

Figure 1:
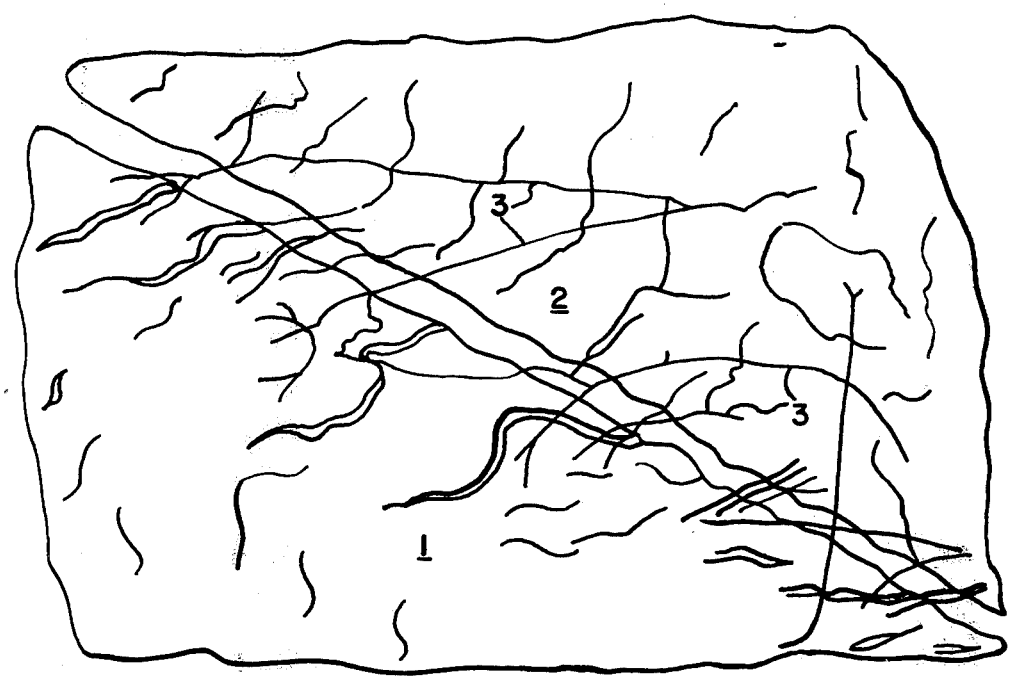
FIG. 1 is a scanning electron microscope photograph, magnified 2600 times, of portions of two adjacent hairs treated with fibrillatable PTFE.

The treatment process according to this invention may be used on any type of hair, but is specifically directed to treating human hair without regard to the history of its previous treatments. For example, the hair may be in its natural condition, tinted or permanently waved, or straightened.

Irrespective of the particular prior treatment to which a mass of hair has been subjected, it is only necessary, for the purposes of this process, that fibrillatable PTFE particles be deposited within the mass of hair in a generally uniform manner, in a condition capable of supporting fibrillation of the particles within the hair, and, that the hair then be subjected to sufficient brushing or rubbing at about or above 40° C., to effect such fibrillation as will permit the hair to be held in place. This process of treating hair, in addition to being useful on living hair, may be used on natural or artificial hair, such as is commonly used for wigs, hair-pieces, toupees, and the like. An improvement in the fullness of natural hair, whether living or not, is noted in all cases utilizing a treatment according to this invention, the hair having a natural appearance, better than if it were not so treated, holding a set over a remarkably long period of time, remaining acceptably clean longer, and, showing good physical and mechanical properties.

In each embodiment of the instant invention, only a fibrillatable form of polytetrafluoroethylene may be used. In particular, the most common form of PTFE is unfibrillatable, granular molding powder, is ineffective in the process of this invention. Similarly, other carbonaceous polymers, such as other polyhalocarbons and polyolefins, silicones, and modifications thereof are ineffective in producing comparable cosmetic characteristics in hair.

The fibrillatable PTFE polymer used in the process of this invention includes the high molecular weight polytetrafluoroethylene resins produced by emulsion polymerization. These PTFE polymers have a broad molecular weight range of about 10 to 20 million and are commercially available products. The preparation of these polymers, which is described in U.S. Pat. No. 2,510,112; U.S. Pat. No. 2,559,752; U.S. Pat. No. 2,587,357 and U.S. Pat. No. 2,685,707 involves well-known emulsion polymerization techniques wherein tetrafluoroethylene under pressure in water containing an emulsifying agent, is reacted with a water soluble free radical catalyst. The emulsion produced is coagulated, washed and then dried. The average agglomerate size of the polymer is about 50 to 560 microns though the primary particle size is in the range less than 1 micron; polymer having larger or smaller average agglomerate size is operative.

The fibrillatable PTFE primary particles formed as described in the prior art are primary particles generally less than $1\mu$ in diameter, and their peculiar propensity for fiber formation has been noted and utilized in U.S. Pat. Nos. 2,613,193; 3,301,807; 3,698,392; 3,838,064; 3,838,092; and 3,864,124.

A fibrillatable form of PTFE is presently restricted mainly to two commercially available types of resin. A first type is a colloidal aqueous dispersion concentrated to about 60 percent by weight of polymer having primary particles from about 0.05 to about 0.5 microns in size, with average diameters of about 0.2 microns. Examples of commercially available polymers of this type are designated Teflon* T-30 and Teflon* K-20 by DuPont, and Fluon GP-1 and Fluon GP-2 by ICI. The second type, often referred to as "fine powder," is obtained by coagulation of the dispersion of primary particles to yield a dry powder of relatively large, spherical, polymeric particles with average diameters of about 450 microns. These dry powders, though fibrillatable, are in a size range which is generally found to be inconvenient to use as a hair grooming aid because they have an undesirable feel and require far too much brushing to produce an acceptable treatment for hair. These drawbacks may be overcome by mechanically breaking up the large polymeric particles into smaller agglomerates of primary particles, as for example, by subjecting a hair grooming aid containing the large particles to an intensive shearing action in a high-speed blender. A third type, which is neither a true colloidal aqueous dispersion nor a fine powder is a coagulated aqueous dispersion known as a "paste polymer." Examples of commercially available PTFE polymers of this type are Fluon** CD-1, CD-014 and CD-042.

* Registered Trademark of duPont de Nemours ** Registered Trademark of ICI

The preferred form of PTFE used in the grooming aid of this invention is a colloidal aqueous dispersion of solid particles present in an amount less than about 5 percent by weight, and preferably less than 1 percent by weight of the liquid or gel phase. It is desirable that the fibrillatable solids be present in low concentration to permit the solids not only to be deposited more or less uniformly in a mass of hair to be groomed, but also to be distributed in a low enough concentration to avoid unnatural clumping of portions of the hair. The particular concentration of PTFE used as a hair grooming aid depends on the compatibility of the particular form of solid PTFE with the liquid grooming aid, and the manner in which the grooming composition is normally used. For example, a relatively large amount, up to about 5 percent by weight, may be used in a liquid, cream or gel shampoo since much of the excess of PTFE will be washed out of the hair. Of course, an even higher concentration may be used, but it will be apparent that it would be uneconomical to do so if the desired benefits may be obtained with lower concentrations.

The PTFE can be used most effectively in any hair preparation that does not incorporate materials which coat the hair with a layer or film to which the PTFE particles or fibers will not readily adhere, such as oils, waxes, and the like. However, even without adhesion of the fibers directly to the strands of hair, the fibers are formed into a network which appears to physically assist in keeping the hair in place. PTFE dispersions which are commercially available at the present time will coagulate in acids and organic solvents such as alcohols. Although this coagulation causes the appearances of such formulations to be unappealing, the products so prepared will be useful if well shaken or otherwise physically mixed before use. This coagulation is believed to be caused by the dispersing agents used in the products and not by the PTFE itself.

As we understand the influence of the solid PTFE particles in grooming hair, the essential fact is that the particles are fibrillated, in situ, so as to generate a random network of microscopic and submicroscopic fibers which are distributed throughout the mass of hair, holding the hair in a loose, natural set, and maintaining the mechanical and elastic natural properties of the hair, while providing it with enhanced body. The particular grooming aid used to introduce the PTFE particles into the mass of hair is not of especial importance so long as the solid particles are dispersible in low concentration more or less uniformly in the hair. A shampoo, hair reducer, tinting solution, and in general, any water-soluble or water-miscible essentially oil-free or lower primary alcohol-free liquid is preferred for forming a mixture with an aqueous dispersion of fibrillatable PTFE particles.

It is not essential that the PTFE be in aqueous dispersion as long as it is easily dispersed in the grooming aid in which it is to be used. Since, at the present time, only aqueous colloidal dispersions of fibrillatable PTFE are available, reference herein is specifically had to this form.

Depending upon the particular mechanical and physical properties desired in the hair to be set, the physical properties of the hair before it is treated, and the conditions and extent to which it is worked, extremely minute quantities of PTFE, no more than trace amounts, may effectively provide the desired results. As explained hereinabove, a hair shampoo with less than 5 percent by weight PTFE, after being washed out of the hair in a normal manner, still leaves an adequate amount of PTFE for the cosmetic purpose of maintaining the hair in place.

It has been found that certain hair grooming aids such as hair tonics, lotions and conditioners which include an alcohol will tend to coagulate an aqueous colloidal dispersion of T-30, Teflon*, with the stabilizers and surfactants presently used. It is expected that a suitable choice of dispersant aids will permit finely divided fibrillatable PTFE to be readily incorporated into an alcohol containing grooming composition.

The actual quantity of a colloidal aqueous dispersion of PTFE which may be in a hair grooming composition may vary widely, though, in general, no more PTFE is used than is required to produce the desired cosmetic effect with a normal application. Thus, though fibrillatable PTFE is a valuable polymer, it is effective in a hair dressing in such a small proportion that it does not contribute significantly to the cost of a hair grooming aid. Particularly since hair treated with PTFE tends to retain a portion of the PTFE even after it is washed, subsequent grooming of the hair may be accomplished with a most sparing use of this novel grooming aid. To this end, a typical grooming aid may include from 0.001 percent to about 1 percent PTFE based on the weight of the non-solid phase, the specific amount used being determined largely by the specific function of the grooming aid.

An important part of this invention is the discovery of means for adding the PTFE to hair to provide an even application of the PTFE particles at very low concentrations (for example, 0.01% by weight of hair) and at concentrations less than, for example, 1% by weight of hair. The higher concentrations will work very well but will mat the hair and leave an obvious excess of white PTFE agglomerates which will brush out to a degree resembling loose dandruff. At levels somewhat below 1% (for example, 0.2% by weight of hair), this latter effect will still persist to some degree.

The optimum results of holding the hair in place and retaining or enhancing the natural appearance of the hair is typically in the range of between about 0.01% and 0.05% of PTFE by weight of hair for most common types of hair.

The preferred formulation which will leave this range of concentration of PTFE in the hair consists of adding an excess of PTFE, for example 5% PTFE by weight of liquid, to any water soluble shampoo. In use, the action of washing hair with such a formulation both cleans the hair, leaving 'squeaky' clean surfaces to which the PTFE fibers will adhere in a relatively even distribution throughout the mass of hair, and removes excess of PTFE particles, resulting in the desired concentrations. Thus, an acceptable concentration of PTFE remains in the hair regardless of the weight and dimensions of the hair being treated, since the retained quantity of PTFE correlates closely with the total surface area of clean hair.

Another formulation which is less convenient than shampoo, but which can be applied to the hair following conventional shampooing, and is especially effective for additions of PTFE between washings, comprises a fibrillatable PTFE added to a water based hair grooming liquid or a suitable cream or gel. This formulation relies upon the user measuring out a quantity of up to two palmfuls of the liquid (about one teaspoon) for men's short hair, and up to three or four times this amount for long, abundant hair. Should the application of PTFE be excessive or uneven, the subsequent step of warm brushing or combing will remove the excess and will result in some redistribution of PTFE in the hair.

The general, PTFE fibrillatable particles may be included in any hair grooming aid which normally requires that the hair be brushed after it is treated. Such grooming aids may include minor amounts of gums, shellac, cellulose ethers, synthetic polymers, proteins and protein hydrolyzates, singly or severally, generally in solution in water, alcohol, or in combined solutions of water such as will not adversely affect the dispersability of the solid PTFE particles in the mass of hair. For the purpose of this invention no distinction is made between a liquid, cream, or gel. A particularly preferred hair grooming aid which may be modified by the addition of T-30 Teflon* fibrillatable PTFE colloidal particles is a shampoo.

Among the numerous liquids useful as a liquid phase carrier for the solid PTFE particles is water. More specifically, a commercial aqueous colloidal dispersion of fibrillatable PTFE, which is diluted so as to contain less than about 5 percent PTFE by weight of liquid, is a surprisingly effective grooming aid. More preferably, a dispersion containing fibrillatable PTFE in the range from about 0.001 to about 1 percent by weight may be used directly on the hair.

A process for treating hair with any of the foregoing hair grooming aids which include PTFE, comprises contacting the hair with the grooming aid and rubbing or brushing the hair at a temperature above the transition temperature at which PTFE fibrillates, and more preferably at about 40° C. or above, until a sufficient quantity of microscopic and submicroscopic fibers are formed to give the hair desirable body and a desirable set. Rubbing may be effected with a towel or a heated surface, such as the surface of a hot water bottle, while the hair is in a damp or dry state. Brushing may be effected either manually or mechanically with any conventional soft, resilient, fiber brush. The direction of brushing the hair is unimportant from the point of fibrillation of the PTFE, but it is preferred to brush the hair after it has been given an initial set, the brushing being effected in such a manner as to build body into the hair and to keep it in the desired set after it has acquired sufficient body. In some instances it may be preferred to brush the hair with a brush combined with a source of gas at an elevated temperature, sometimes referred to as styling brushes, particularly where accelerated fibrillation is desired. Fibrillation is effected most efficiently when the hair is in a dry, nearly dry or damp condition. Wet hair containing the grooming aid of this invention combs out freely and untangles easily but the wetness impedes fibrillation of the PTFE. Though it is possible to fibrillate PTFE particles in wet hair, with much effort under the most favorable conditions, it is generally impractical to do so except by brushing hair which has been wet with hot water, for example, in a shower bath. In general, the application of the hair grooming aid of this invention which includes PTFE, is essentially the same as that of the same grooming aid which does not contain the PTFE resin, except that it is rubbed or brushed after the hair is dry or nearly dry, until the desired effect, due to the presence of the PTFE, is obtained. For brushing the hair, a relatively soft bristle brush is preferred.

The following examples serve more clearly to illustrate the invention:

EXAMPLE 1

A shampoo such as is conventionally used, either in the form of a liquid, for example, Head and Shoulders$^R$, or in the form of a gel which may be squeezed from a tube, for example, Prell$^R$, is formulated with 5 parts by weight solid PTFE in 100 parts by weight liquid. Thus, in 100 grams of shampoo, approximately 9 parts by weight of 60% solids T-30 colloidal aqueous dispersion of PTFE are used. A small portion of the shampoo, as much as is conventionally used, is placed in the palm of the hand and rubbed into wetted hair until the desired sudsing or shampooing action is obtained. The hair is thereafter washed in a conventional manner to cleanse the hair to a "squeaky" cleanness, recognizing that some, and possibly a major proportion of the PTFE solids in the hair is washed away leaving an effective concentration of PTFE.

The washed hair is then damp-dried with a towel, combed, set in the desired style and permitted to dry at room temperature in the usual manner. After the hair dries, it is warmed by a heat lamp and brushed repeatedly with a soft bristle brush until the desired body and obedience is obtained. Generally, fibrillation of the PTFE particles is evidenced by a slight but noticeable drag on the bristles of the brush. The same effect may be obtained when the hair is still damp or nearly dry, except that damp hair is preferably brushed at an elevated temperature. It is found that the treated, brushed hair has been imbued with a desirable luster and softness, and enhanced body and elasticity, such as is a characteristic of natural, healthy hair; yet, treated hair unlike untreated hair, maintains its set, stays acceptably clean longer, and can be repositioned with brushing.

Alternatively, the shampooed and cleansed wet hair may be wet combed and set, and dried under a hair drier until damp or dry. It is thereafter brushed repeatedly while the hair is warm, combing it intermittently if desired to mold it, until the hair acquires the characteristics of body, feel and maintenance of the set as described hereinbefore.

It is thought that additional washing of the hair treated as described hereinabove does not entirely remove the PTFE previously added or the fibers formed in a prior grooming. In other words, a residue of fibers remains in the hair so that subsequent groomings may show improved results which typically level off after three or four groomings. Though difficult to measure, it is found that the amount of solid PTFE present as fibers in the hair after it is shampooed, cleaned and set is generally less than 0.01% by weight. There is no critical amount that we are able to determine, either as a lower limit or as an upper limit. It is readily apparent that an excess of PTFE fibrillated in the hair produces an overly dense "mat" of hair which looks unnatural. At the other extreme, only a trace of PTFE may provide a noticeable effect in baby fine hair, particularly where the hair lacks body. In the shampoo described hereinabove, a user quickly can determine for himself a personal preference for the extent to which his or her hair should be treated to look natural and attractive.

EXAMPLE 2

A commercially available aqueous colloidal dispersion of T-30 Teflon* fibrillatable PTFE, having a concentration of about 60 percent by weight solids, is diluted with distilled water so as to provide a grooming aid which contains 1 part by weight PTFE solids and 100 parts liquid. This dilution negates sudsing of the grooming aid which may be used directly on the hair.

About one-half teaspoonful of the grooming aid, sufficient for a man's short cut hairstyles, is smeared on the palms of a user's hands and rubbed into the hair on his head. No sudsing is evident due to the presence of dispersant aids in the liquid. The hair is combed, molded or brushed into a predetermined style and thereafter further brushed until a desirable fullness and "spring" is imparted to the hair. Surprisingly the hair maintains the set for a long time, and despite normal sleeping on the set hair, it recovers remarkably well, particularly if it is given an additional brushing.

It will be recognized that in the disclosure hereinabove, reference is made to a fibrillation temperature of at least about 20° C. This temperature is deemed to be a minimum temperature of fibrillation for currently marketed fibrillatable PTFE resins. Other PTFE resins may be fibrillatable at temperatures below 20° C. The critical requirement is that the PTFE resin be used at a temperature above that required to cause fibrillation. The most rapid fibrillation occurs at a comfortable warmth of from about 40° C. to about 60° C. Higher temperatures will work better, but are not practical nor comfortable.

If desired, fragrances and the like may be added to the foregoing aqueous grooming aid.

Figure 2:
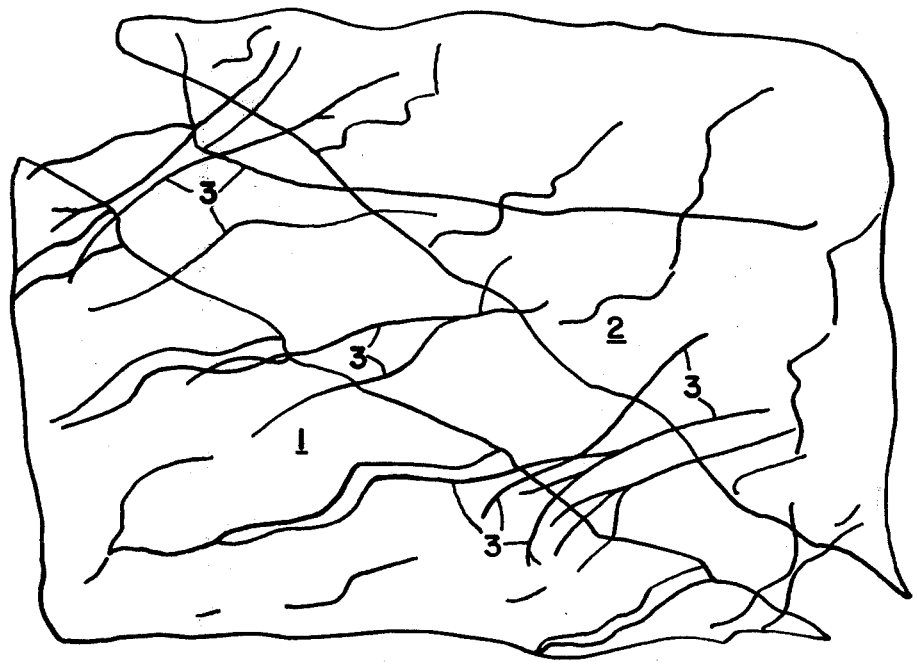
FIG. 2 is a scanning electron microscope photograph of a portion of the treated hairs shown in FIG. 1, magnified 12,000 times, clearly showing a network of PTFE fibers bridging the hairs.

Referring now to the microphotographs, two strands of hair are seen in FIG. 1 extending diagonally across the photograph. The hair was freshly washed with a shampoo containing a small amount of fibrillatable PTFE. The PTFE was then fibrillated using conventional techniques after which the photographs were made using an electron microscope. The strands of PTFE are barely visible under 2600X magnification and of course are invisible to the naked eye. They can be seen a little more clearly in FIG. 2 are are shown in a web-like arrangement with one another, binding the individual strands of hair together in a fibril network.

Modifications, changes, and improvements to the preferred forms of the invention herein disclosed, described, and illustrated may occur to those skilled in the art who come to understand the principles and precepts thereof. Accordingly, the scope of the patent to be issued hereon should not be limited to the particular embodiments of the invention set forth herein, but rather should be limited by the advance by which the invention has promoted the art.

What is claimed is:

1. A hair grooming aid consisting essentially of a shampoo and between about 0.001% and about 5% by weight of fibrillatable polytetrafluoroethylene resin particles dispersable or dispersed therein, wherein the primary particle size is in the range of less than about 1 micron in diameter.

* * * * *